US00PP33720P2

(12) United States Plant Patent
Bacon et al.

(10) Patent No.: US PP33,720 P2
(45) Date of Patent: Dec. 7, 2021

(54) PLUM TREE NAMED 'SUPLUM59'

(50) Latin Name: *Prunus salicina*
Varietal Denomination: Suplum59

(71) Applicant: Sun World International, LLC, Bakersfield, CA (US)

(72) Inventors: Terry A. Bacon, Bakersfield, CA (US); Terrence J. Frett, Bakersfield, CA (US)

(73) Assignee: Sun World International, LLC, Bakersfield, CA (US)

( * ) Notice: Subject to any disclaimer, the term of this patent is extended or adjusted under 35 U.S.C. 154(b) by 0 days.

(21) Appl. No.: 17/202,885

(22) Filed: Mar. 16, 2021

(51) Int. Cl.
*A01H 5/08* (2018.01)
*A01H 6/74* (2018.01)

(52) U.S. Cl.
USPC ..... Plt./184
CPC ..... *A01H 6/7472* (2018.05)

(58) Field of Classification Search
USPC ..... Plt./184
CPC ..... A01H 6/7472; A01H 5/08
See application file for complete search history.

*Primary Examiner* — Keith O. Robinson
(74) *Attorney, Agent, or Firm* — Knobbe, Martens, Olson & Bear, LLP

(57) ABSTRACT

A new and distinct variety of plum tree, *Prunus salicina*, cv. 'Suplum59', is characterized by having fruit that is very large, with reddish-black skin and yellow flesh that ripens late in the season. The fruit of the new variety 'Suplum59' also has firm flesh, a very sweet flavor and a stone that is adherent to the flesh.

1 Drawing Sheet

Latin name of the genus and species claimed: *Prunus salicina.*

Variety denomination: 'SUPLUM59'.

BACKGROUND AND SUMMARY OF THE INVENTION

This application relates to the discovery and asexual propagation of a new and distinct variety of plum tree, *Prunus salicina* cv. 'Suplum59'. The new variety was first originated by hybridization and identified in September 2016 by Terry A. Bacon and Terrence J. Frett as breeder number 'PL2014YB'.

The seed parent is 'PL968RB' (unpatented breeding selection), and the pollen parent is unknown (from a bulk pollen of unpatented breeding program selections). The parent varieties were first crossed in March 2013, the date of first sowing being March 2014 and the date of first flowering being March 2016. The new plum variety 'Suplum59' was first asexually propagated by Terry A. Bacon and Terrence J. Frett near Wasco, Kern County, Calif. in February 2017 by dormant grafting.

The new variety 'Suplum59' is characterized by having fruit that is very large, with reddish-black skin and yellow flesh that ripens late in the season. The fruit of the new variety 'Suplum59' also has firm flesh, a very sweet flavor and a stone that is adherent to the flesh.

The new variety 'Suplum59' resembles its seed parent 'PL968RB' (unpatented breeding selection) in that both have fruit with reddish-black skin. However, the fruit of the new variety 'Suplum59' has yellow flesh compared to red flesh for 'PL968RB' and begins ripening about 48 days later than the fruit of 'PL968RB'. Further, the fruit of the new variety 'Suplum59' has a higher brix at 22% compared to about 20% for 'PL698RB'.

The new variety 'Suplum59' has black skin and yellow flesh like 'Suplumsix' (Plant Pat. No. 2,747), 'Suplumthirtysix' (Plant Pat. No. 19,023) and 'Owen-T' (unpatented) but the fruit of the new variety 'Suplum59' begins ripening about 3 days later than the fruit of 'Suplumsix', 11 days later than 'Suplumthirtysix' and 61 days later 'Owen-T'. Further, the fruit of the new variety 'Suplum59' has a larger size at about 150 g compared to fruit of about 124 g for 'Suplumsix' and a smaller size compared to the fruit of 'Suplumthirtysix', about 195 g and the fruit of 'Owen-T', about 170 g. The fruit of the new variety has a higher brix at 22% compared to 18% for 'Suplumsix', 19% for 'Suplumthirtysix' and 16% for 'Owen-T'.

The fruit of the new variety 'Suplum59' has reddish-black skin like 'Suplumfifty' (Plant Pat. No. 27,327), but it has yellow flesh, unlike the red flesh of the fruit of 'Suplumfifty'. The fruit of the new variety 'Suplum59' begins ripening about 27 days later than 'Suplumfifty', and it has higher brix at 22% compared to 20% for 'Suplumfifty'.

The new variety 'Suplum59' has been shown to maintain its distinguishing characteristics through successive asexual propagations by, for example, cuttings and grafting.

BRIEF DESCRIPTION OF THE PHOTOGRAPH

The accompanying color photographic illustration shows typical specimens of the foliage and fruit of the peach variety 'Suplum59'. The illustration shows the upper and lower surfaces of the leaves and exterior and sectional views of the fruit. The photographic illustration was taken shortly after the fruit was picked and the colors are as nearly true as is reasonably possible in a color representation of this type.

DETAILED DESCRIPTION

Throughout this specification, color names beginning with a small letter signify that the name of that color as used in common speech is aptly descriptive. Color names beginning with a capital letter designate values based upon The R.H.S. Colour Chart published by The Royal Horticultural Society, London, England, 1986.

The descriptive matter which follows pertains to three-year-old 'Suplum59' plants grown in the vicinity of Wasco, Kern County, Calif. during 2020 and is believed to apply to plants of the variety grown under similar conditions of soil and climate elsewhere.

TREE

General: (Measurements taken on three-year-old trees unless otherwise noted).

*Size.*—Medium: reaches a height of approximately 3 meters with normal pruning.

*Habit.*—Upright.

*Vigor.*—Medium.

*Productivity.*—Productive.

*Bearer.*—On spurs and long shoots.

*Fertility.*—Self-incompatible; requires pollinator.

*Hardiness.*—Hardy in all fruit growing areas of California. Winter chilling requirement is approximately 700 hours at or below 7.2° C.

*Disease resistance/susceptibility.*—Under close observation in Kern County, Calif., no particular plant/fruit disease resistance/susceptibility has been observed.

*Insect resistance/susceptibility.*—Under close observation in Kern County, Calif., no particular plant/fruit insect resistance/susceptibility has been observed.

Trunk: (Measurements taken at approximately 30 cm above soil line on mature tree).

*Diameter.*—Approximately 14 cm.

*Texture.*—Medium shaggy, increasing with age of tree.

*Trunk color.*—About Medium Greyed-Orange 166B, becoming darker with age.

Branches: (Measurements taken at approximately 90 cm above soil line).

*Size.*—Diameter approximately 7 cm.

*Texture.*—Medium shaggy, increasing with age.

*Color.*—About Dark Grey 201B with highlights of about Medium Grey-Brown 199B, becoming darker with age.

*Lenticels.*—Present.

*Lenticels density.*—Plentiful, about 50/cm$^2$.

*Lenticels color.*—About Medium Greyed-Green 197C.

*Lenticels dimensions.*—Length: approximately 1-3 mm. Width: approximately 0.5 mm.

One year old shoots: (Data taken in September at mid-point of current-season growth).

*Size.*—Average diameter approximately 5 mm.

*Topside color.*—About Medium Green 137C, becoming Medium Greyed-Orange 165B by September.

*Underside color.*—About Medium Green 137C, becoming Medium Greyed-Orange 165B by September.

*Internode length.*—Approximately 20 mm. Midway on shoot.

*Lenticels color.*—About Medium Greyed-Green 197C.

*Lenticels size.*—Very small, difficult to see, about 0.2 mm diameter.

*Lenticels density.*—Medium.

*Spur length.*—Medium, usually 8 mm.

*Anthocyanin intensity on upper side of shoot.*—Very sparse.

Vegetative buds:

*Position of vegetative bud in relation to shoot.*—Slightly held out.

*Size.*—Medium, approximately 1.5 mm wide×2.5 mm long.

*Shape.*—Conical.

*Bud shape at apex.*—Acute.

*Color.*—About Dark Greyed-Orange 166A.

Flower buds:

*Shape.*—Ovoid.

*Dimensions.*—Approximately 1.1 mm wide×2 mm long.

*Color.*—About Medium Greyed-Orange 177B.

*Distribution.*—2-6 buds, generally on spurs and one-year old shoots.

*Ratio of flowering buds to vegetative buds.*—2-6 flower buds to 1 vegetative bud.

FOLIAGE

Leaves: (Data taken in July on fully expanded leaves at mid-point of the current season growth).

*Average length.*—Medium; approximately 8.8 cm without petiole.

*Average width.*—Medium; approximately 4 cm.

*Length/width ratio.*—Moderately elongated; about 2.0:1.

*Shape.*—Elliptic.

*Color.*—Upper surface: About Dark Green 139A. Lower surface: About Medium Green 136C.

*Glossiness of upper side.*—Medium.

*Angle at apex* (*excluding tip*).—Acute.

*Shape of base.*—Acuminate.

*Vein color.*—About Light Green 139D with highlights of Medium Greyed-Orange 176C where exposed to sun.

*Venation.*—Pinnately net veined.

*Surface texture.*—Smooth on both upper and lower surfaces.

*Shape in the cross section.*—Concave.

*Profile.*—Up folded.

*Leaf blade tip.*—Curved downwardly.

*Undulation of margin.*—Slight.

*Density of pubescence of lower side.*—Absent or very sparse.

*Incisions of margin.*—Bi-crenate.

Petiole:

*Average length.*—Medium; approximately 12 mm.

*Average diameter.*—Approximately 1.5 mm.

*Color.*—About Light Green 139D with highlights of Medium Greyed-Orange 176C where exposed to sun.

Stipules:

*Number/leaf bud.*—Usually two.

*Typical length.*—Approximately 3 mm.

*Color.*—About Dark Greyed-Orange 166A when dried.

*Persistence.*—Falls off.

Leaf glands:

*Average number and arrangement.*—2-4, alternating. Predominately on petiole.

*Form.*—Globose.

*Diameter.*—Approximately 0.3 mm.

*Color.*—About Medium Greyed-Yellow 162A becoming Dark Greyed-Orange 166A over time.
*Positions of nectarines (glands).*—Predominately on base of leaf blade.

FLOWERS

General:
*Time of beginning of flowering.*—Very late for the San Joaquin Valley, Calif.
*Flower blooming period.*—First bloom: Approximately March 1 in Wasco, Calif. Full bloom: Approximately March 11 in Wasco, Calif.
*Location of first bloom.*—Tips of one-year old shoots.
*Location of full bloom.*—Central part of the tree canopy.
*Duration of bloom.*—Approximately 10 days.
*Flower diameter.*—Medium, approximately 1.8 cm.
*Flower form.*—Showy.
Pedicels:
*Length.*—Long, approximately 12 mm.
*Diameter.*—Approximately 1.2 mm.
*Color.*—About Light Green 138C.
*Pubescence.*—Absent.
Petals:
*Number.*—5.
*Arrangement.*—Slightly overlapping.
*Color.*—About White 155A.
*Length.*—Medium, approximately 7.8 mm.
*Width.*—Approximately 7.9 mm.
*Shape.*—Circular.
*Apex shape.*—Rounded.
*Base shape.*—Narrows at point of attachment.
*Surface texture.*—Smooth.
*Undulation of margins.*—Medium.
*Frequency of flowers with double petals.*—None.
*Claw.*—Absent.
Sepals:
*Number.*—5.
*Length.*—Approximately 4 mm.
*Width.*—Approximately 3 mm.
*Shape.*—Triangular.
*Color.*—About Light Green 138C.
*Surface texture.*—Smooth.
*Margins.*—Undulating.
*Positioning.*—Adpressed to petals.
*Frequency of flowers with double sepals.*—None.
Stamens:
*Number.*—About 24-30; usually 28.
*Average length.*—Variable, ranging from 3 mm to 10 mm.
*Filament color.*—About White 155A.
*Flower pollen color.*—About Light Yellow-Orange 18A.
*Position.*—Perigynous.
Pistil:
*Average length.*—Approximately 3-4 mm.
*Ovary diameter.*—Approximately 2.2 mm.
*Pubescence.*—Absent.
*Stigma extension in comparison to anthers.*—Usually below.
*Style frequency of supplementary pistils.*—Few.
Rceptical:
*Depth.*—Medium, approximately 4 mm.
*Pubescence of inner surface.*—Absent.
*Pubescence of outer surface.*—Absent.

FRUIT

General: (Description taken at firm-mature near Wasco, Kern County, Calif.).
Ripening:
*Time of beginning of fruit ripening.*—Late season.
*Date of first pick.*—Approximately September 5.
*Date of last pick.*—Approximately September 15.
Size:
*Height.*—Tall, approximately 65 mm.
*Diameter in line with suture plane.*—Approximately 65 mm.
*Diameter perpendicular to suture plane.*—Broad, approximately 66 mm.
*Average weight.*—Very large, approximately 150 g.
Peduncle:
*Length of stem.*—Short; approximately 7 mm.
*Diameter of stem.*—Approximately 3 mm.
*Color of stem.*—About Light Green 139D.
Shape:
*Viewed from apex.*—Circular.
*Viewed in-line with suture.*—Circular.
*Viewed from side, perpendicular to suture.*—Circular.
*Symmetry.*—Symmetric or slightly asymmetric.
*Shape of base.*—Pointed.
*Shape of apex.*—Depressed.
Fruit stem cavity:
*Depth of stalk cavity.*—Shallow; Approximately 5 mm.
*Width of stalk cavity.*—Medium; Approximately 10 mm.
*Depth of suture.*—Absent or very shallow.
Fruit skin:
*Thickness.*—Medium; typical of most varieties.
*Flavor.*—Mild.
*Adherence to flesh.*—Strong.
*Surface texture.*—Smooth.
*Pubescence.*—None.
*Bloom on skin.*—Weak.
*Ground color.*—Not visible.
*Overcolor.*—About Dark Greyed-Purple 187A.
*Relative area of overcolor.*—Whole surface.
*Pattern of overcolor.*—Solid.
*Reticulation.*—Absent.
*Tendency to crack.*—Rare.
*Number of lenticels.*—Medium, small and difficult to see. About 10/cm$^2$.
*Size of lenticels.*—Very small, approximately 0.2 mm.
Flesh at firm-mature harvest stage:
*Ripens.*—Evenly.
*Texture.*—Crisp-juicy.
*Flavor.*—Very sweet, subacid, about 55 Brix:Acid.
*Color.*—About Medium Yellow-Orange 18C.
*Firmness.*—Firm; typically 8 lb pressure at harvest.
*Juice.*—High; able to squeeze free juice easily.
*Acidity.*—Low; 0.40% titratable acidity.
*Sweetness.*—High; about 22% Brix at harvest.
*Adherence to stone.*—Adherent.
*Amount of fiber.*—Medium.

Fruit use: Fresh market.

Fruit shipping and keeping quality: Good.

Stone:

*Stone freeness.*—Cling.

*Stone size.*—Size: Medium. Length: Approximately 21 mm. Diameter in line with suture plan: Approximately 18 mm. Diameter perpendicular to suture plane: Approximately 9 mm.

*Color.*—About Medium Greyed-Orange 170B when dried.

*Position of maximum diameter.*—Middle.

*Shape from lateral view.*—Medium elliptic.

*Shape from ventral view.*—Narrow elliptic.

*Shape from basal view.*—Narrow elliptic.

*Base shape.*—Nearly straight.

*Apex shape.*—Pointed.

*Stone ridges.*—Rounded throughout.

*Stone outgrowing keel.*—Partially developed.

*Ventrical edge.*—Thin with slight wing toward middle.

*Dorsal edge.*—Narrow, shallow grooves throughout.

*Fibers.*—Not visible.

*Symmetry in lateral view.*—Symmetrical or slightly asymmetrical.

*Texture of lateral surface.*—Slightly rough.

*Width of stalk-end.*—Medium.

*Tendency to split.*—Rare.

What is claimed is:

1. A new and distinct variety of plum tree as herein described and illustrated.

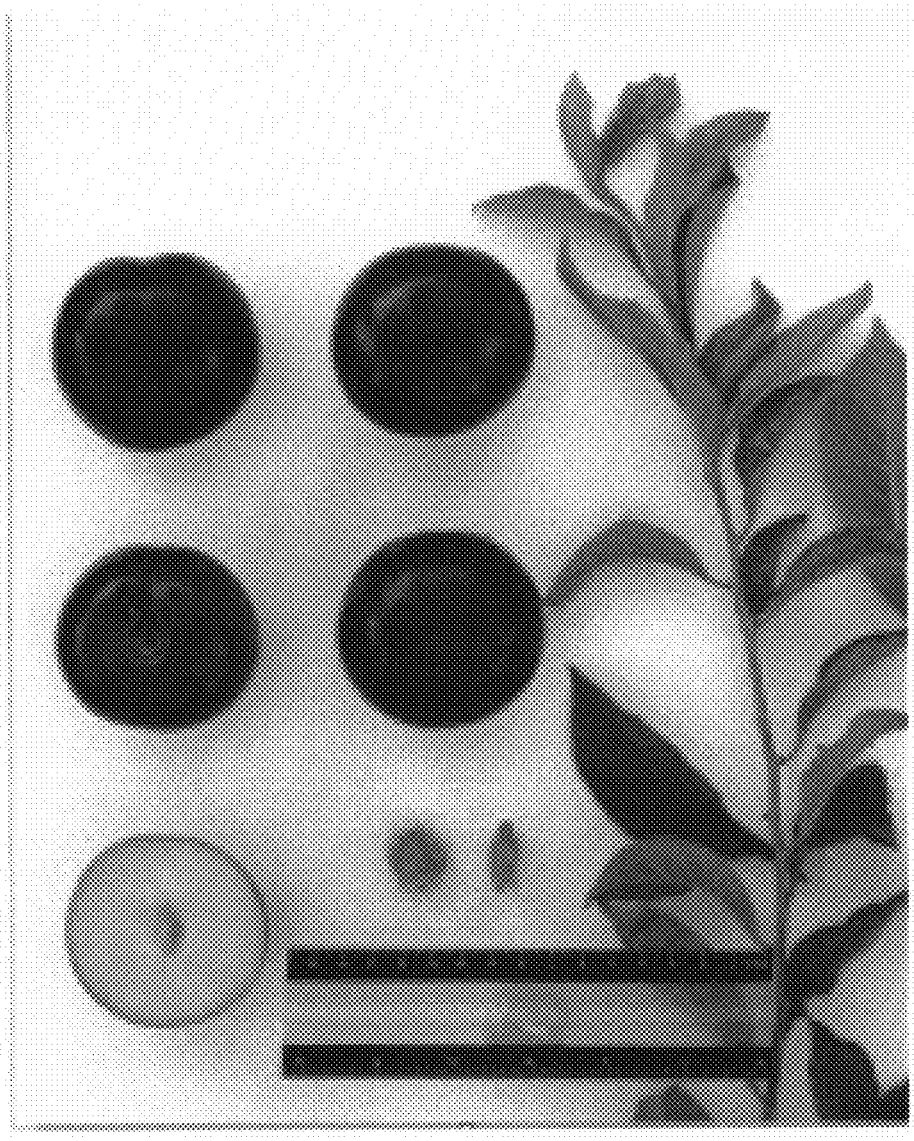

* * * * *